FOUR LEAF CLOVER PLANT
Filed Feb. 22, 1973 2 Sheets-Sheet 1
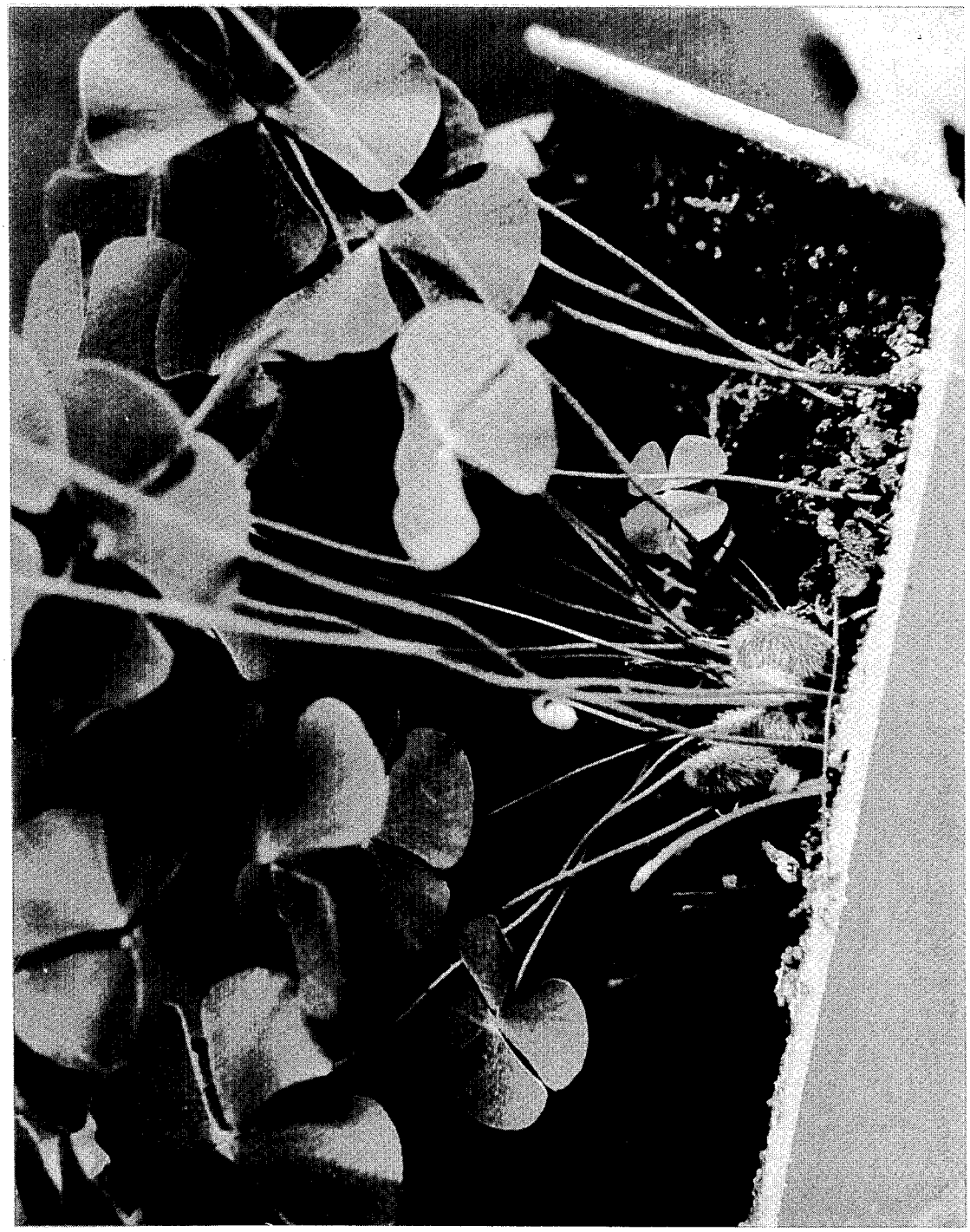

FOUR LEAF CLOVER PLANT
Filed Feb. 22, 1973 2 Sheets-Sheet 2
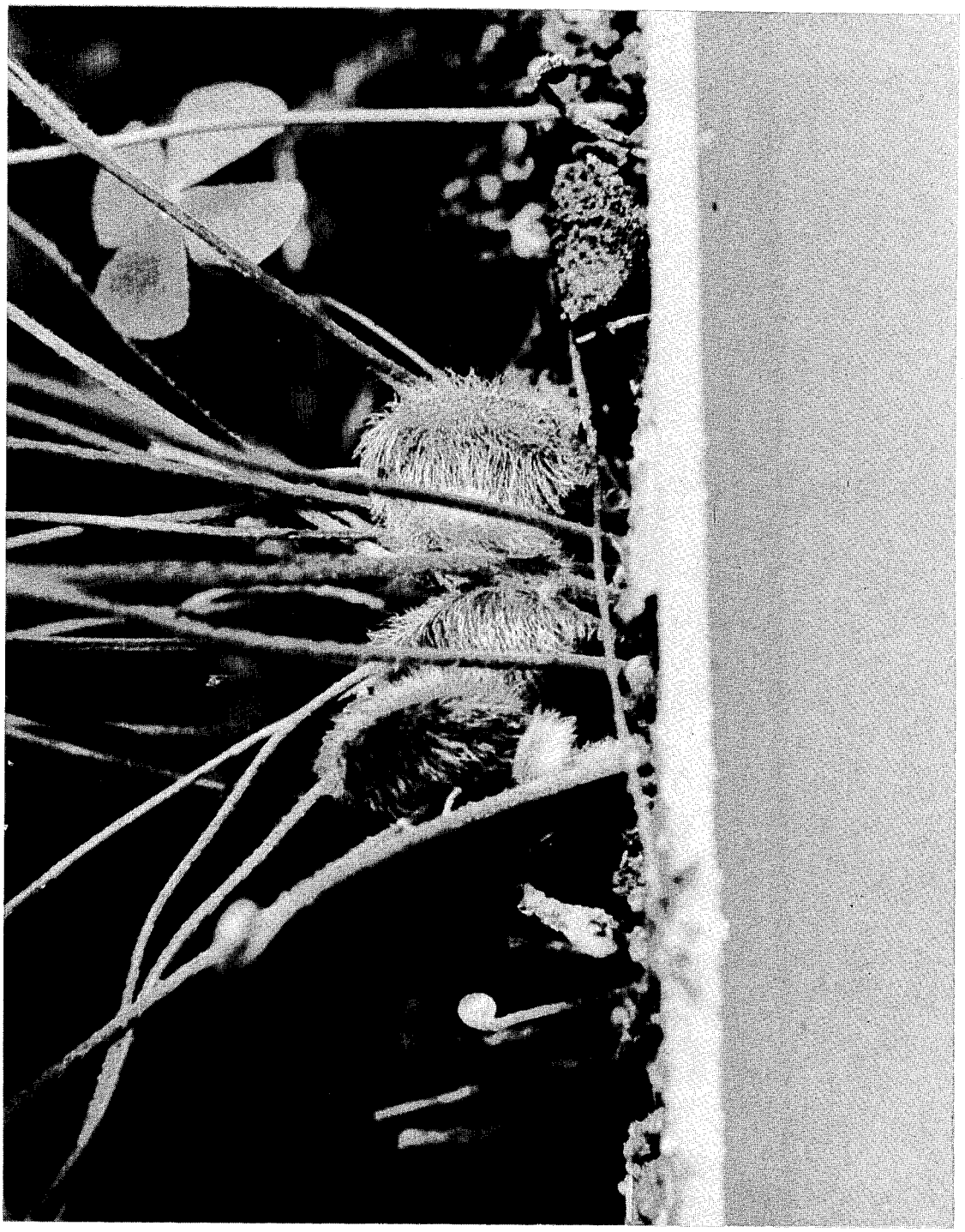

United States Patent

Plant Pat. 3,730
Patented June 17, 1975

3,730
FOUR LEAF CLOVER PLANT

Ellis H. Dearing, Tulsa, Okla., assignor of fractional part interest to Otto Duane Terrell, Norco, Calif.

Substituted for abandoned plant patent application Ser. No. 843,123, Aug. 6, 1969. This application Feb. 22, 1973, Ser. No. 334,661
Int. Cl. A01h 9/00
U.S. Cl. Plt.—88 1 Claim The present invention relates to a new and distinct variety of pepperwort which was discovered by me in a flower bed located in a private yard. The new variety is a pepperwort or water clover, member of the genus Marsilea, which is large, and capable of growing in soil of ordinary moisture content.

At the time of my discovery, the plant was apparently growing voluntarily in a flower bed containing a variety of plants, and it was thought that the plant was a result of a combination of running buffalo clover, *Trifoleum repens* family and fernroot of the pepper wort family. The fact that all of the stems of the plant contained four leaves attracted my attention. Upon a close inspection of this particular plant and through cultivation, work, and tests, therewith, I have discovered that it apparently is a species of Marsilea or water clover which is known to grow only in water or in very damp or wet muds.

I watched the plant carefully and during the first year the plant was located in the out-of-doors, growing in the usual or common dry soil in the area of the yard. The second year, the original plant was planted in a container and placed indoors and located particularly on a window ledge. The plant grew and flourished, with only the normal or usual quantity of watering as might be used on a house plant, and not with any abnormally great quantity of watering. During the third year it was possible to take a first transplant. During the third year one transplant was placed in the out-of-doors and a second transplant was placed indoors. Again, only a normal quantity of water was applied to the plant, and no attempt was made to maintain the plant in water or in wet mud.

Continued observations and work with the plant and progeny thereof from root transplants have convinced me that a new and improved variety of Marsilea has been discovered which is distinctly different from all other varieties with which I am familiar, as evidenced by the following unique combination of characteristics which are outstanding in my new variety:

1. Plants bear a general similarity in appearance to a clover plant variety but each stem of the plant has four leaflets.

2. Plants growing out-of-doors in a natural soil rather than in water or abnormally wet surroundings.

3. Plants growing out-of-doors have a natural dying out during freezing temperatures but come back in the spring of the year with the return of warmer temperatures.

4. Plants grown indoors flourish in natural soil with out excessive use of water.

5. Plants grown indoors do not go through any natural dying out process but continue in their growth.

6. Whereas the plants flourish in wet soil, they also flourish equally well in shady soil, dry soil, sunny soil, and substantially any type of soil with the exception of clay.

Successive reproductions of my new Marsilea variety as performed by me shows that a continued production of four leaflets on each stem is fixed and established and come true with succeeding propagations, with the plants bearing a strong resemblance to clover.

The accompanying drawings show a typical bed containing typical specimens of the new plant of the Marsilea family; one drawing shows the entire plant and the other drawing shows an enlargement of the sporocarps.

The following is a detailed description of my new Marsilea variety, as based on observations of specimen plants:

Origin: Newly discovered form of Marsilea.

Propagation: Holds its distinguishing characteristics through succeeding propagations by root transplant.

Stems: Slender horizontal rhizomes.

Leaves: Alternate, fascicled. Petioles 10–20 cm. long, sparsely short pilose with white trichomes; leaflets cuneate-flabelliform, 2–3 cm. long, entire, pilose, to sparsely pilose on the outer (abaxial) side with long slender tapering white more or less erect trichomes, and strigose with the other short proximally pointing arm of the same trichome, the inner (idaxial) surface similarly but more sparsely vestite, both arms of the trichomes shorter, the distal margin with abundant white short curving trichomes; junction of petiole and bases of the leaflets densely short white pilose; peduncles ca. 1 cm. long, fused with the petioles for 3 cm.

Sporocarps: Solitary on the peduncles, ca. 1 cm. long, lenticular-ellipsoidal, densely hirsutulose with transversely downwardly directed hairs at first white, becoming reddish brown at maturity; raphe ca. 2 mm. long; lower hook (at summit of peduncle) a mere papilla ca. ⅓ mm. high, the upper hook obsolete.

Sori: 11 on each side; megasporangia 3–8 per sorus.

Discussion: The specific identity of this plant is uncertain. It may well be the European *Marsilia quadrifolia,* but that usually has 2 or more sporocarps per peduncle, though Hegi, Illustrierte Flora von Mittel-Europa, zweite Auflage, Vol. 1, Tafel 8, illustrates it with only one. The subject plant bears 2 sporocarps, both solitary. It is similar to *M. marcropoda* which has 2–6 sporocarps on each peduncle as described, Correll and Correll, Aquatic and Wetland Plants of Southwestern United States, p. 55, 1972.

I claim:

1. A new and distinct variety of pepperwort characterized by its ability to grow in soil of ordinary water content, and great robustness.

No references cited.

ROBERT E. BAGWILL, Primary Examiner